United States Patent [19]

Commisso et al.

[11] Patent Number: 5,027,455
[45] Date of Patent: Jul. 2, 1991

[54] MULTIPOSITION MISTING LOUNGING PAD

[76] Inventors: Louis Commisso, 3807 N. 30th St.-#22; Gary D. Hawkins, 6131 N. 16th St. #D-102, both of Phoenix, Ariz. 85016

[21] Appl. No.: 483,661

[22] Filed: Feb. 23, 1990

[51] Int. Cl.⁵ .............................................. A47G 9/06
[52] U.S. Cl. .............................................. 5/421; 5/417; 5/420; 239/289
[58] Field of Search .......................... 5/417, 420, 421; 297/180; 239/289; 128/366, 376

[56] References Cited

U.S. PATENT DOCUMENTS

| | | | |
|---|---|---|---|
| 3,336,610 | 8/1967 | Geddings | 5/420 |
| 3,688,775 | 9/1972 | Raymann | 239/289 X |
| 3,997,927 | 12/1976 | Culligan | 5/421 X |
| 4,151,618 | 5/1979 | Carpenter | 5/421 X |
| 4,648,143 | 3/1987 | Breaux et al. | 5/421 X |
| 4,765,542 | 8/1988 | Carlson | 239/289 |
| 4,846,525 | 7/1989 | Manning | 239/289 X |

Primary Examiner—Michael F. Trettel

[57] ABSTRACT

A misting device, usable with a lounging pad, produces a gentle blanket-like mist that completely covers sunbathers and provides cooling to keep a person comfortable while sunbathing without having to move away from the device. The misting device is removably attachable to a lounge pad and has mist emitting heads which are individually rotatable to control the direction of mist emission. While the device is attached to a lounge pad, the lounge pad may be folded for transport or to conform to the shape of lounge chairs or ground surface contours.

2 Claims, 1 Drawing Sheet

MULTIPOSITION MISTING LOUNGING PAD

FIELD OF INVENTION

This invention relates to a recreational device for cooling the human body by use of a multiposition misting lounging pad for sunbathing, lounging, and the like.

BACKGROUND OF THE INVENTION

The need to effectively provide for cooling off and staying comfortable during sunbathing is well known. Traditionally, various methods have been used such as; hand held spray bottles, spray nozzle attached to garden hose, and attachable and internal spray systems for lounge chairs. Thus, those who sunbathe, will appreciate an easy to use recreational sunbathing device and enjoy a safe and efficient method of cooling. It is to these ends that our invention is directed.

OBJECTS OF THE INVENTION

It is the object of our invention to provide an on-demand multiposition misting lounging pad for sunbathers.

Another object of our invention is to provide a multiposition misting lounging pad for sunbathers that is simple and economical to manufacture.

In another aspect, the third object of our invention is to provide a multiposition misting lounging pad that can be used without the necessity of installation or assembly by the consumer.

SUMMARY OF THE INVENTION

Briefly, these and other objects of our invention are achieved by a multi position lounging pad equipped with a misting device for sunbathing and the like including a swivel hose adapted and value combination, for affixing a common garden hose to the misting device. A valve, with a regulating lever is used to regulate the flow of water into the misting device. The swivel hose adapter and valve combination are the control means for said device. The tubing valve adapter is used for connecting the polyethylene tubing to the valve. 360 degree horizontal rotatable misting heads are attached at predetermined locations along the length of the polyethylene tubing. At the opposite end of the tubing there is a end cap connector that can be removed for flushing misting device.

After a common garden hose is attached and turned on a person lying on the multiposition misting lounging pad has the option to be covered by a fine gentle blanket of cooling mist regulated by the flow of water into the misting system via the valve lever located on the valve. During misting the sunbather can change the direction of the mist by simply hand rotating the individual misting head or all heads together.

The invention may be summarized as a misting device which may be used in combination with a lounge pad. There is disclosed a compression fitting having a first end for coupling to a source of pressurized liquid, and an output end compressively coupled to a length of liquid conduit tubing. A selected length of liquid conduit tubing has an input end coupled to the output end of the compression fitting and a sealed distal end to preclude the exit of liquid therefrom.

A misting head is coupled to the length of liquid conduit tubing for emitting a fine, gentle mist when a pressurized source of liquid is coupled to the tubing. There are means coupled to the liquid conduit tubing and adapted for adjustably coupling the misting device to a lounge pad having a length and width.

The liquid conduit tubing has a selected length generally equivalent to one-third the length of a lounge pad to which the misting device is to be coupled. In addition there are disclosed means for rotatingly coupling the misting head to the liquid conduit tubing whereby the direction of the emission of mist from the head may be selectably controlled.

Preferably, a plurality of the misting heads are rotatingly coupled to the liquid conduit tubing. Disclosed, also, are means for unsealing the distal end of the liquid conduit tubing whereby the tubing may be flushed when connected to a source of pressurized liquid; and filter means coupled to the liquid conduit tubing to preclude the entry of particulate matter into the tubing.

Finally, the disclosure includes a lounge pad, foldable in increments of one-third its length, coupled to the liquid conduit tubing, the pad remaining foldable in one-third increments thereafter.

The invention may also be characterized as an improvement in the combination of a lounging pad, on which a person may rest at least a part of his body, and a liquid spray device for spraying a person reclining on the pad, the liquid spray device being coupled along one side of the pad. The improvement is disclosed wherein the pad is foldable into sections for ease of transport and storage. The liquid spray device is coupled along the side of one of the sections into which the pad is foldable and has a length generally equivalent to a side dimension of the section. Thus the pad may be folded for ease of transport and storage while the spray device is still coupled along the side of the one section.

The liquid spray device is, itself, a misting device which comprises a selected length of liquid conduit tubing. There is a misting head coupled to the tubing for emitting therefrom a fine, gentle mist when a pressurized source of liquid is coupled to the tubing. Means are provided for adjustably coupling the misting device to the lounge pad.

The improvement is enhanced by means for rotatingly coupling the misting head to the liquid conduit tubing, and by means for rotatingly coupling the liquid conduit tubing to a source of pressurized liquid, such that the direction of the emission of mist form the head may be selectably controlled.

DESCRIPTION OF DRAWING

The subject matter of the invention is particularly pointed out and distinctly claimed in the concluding portion of the specification. The invention, however both as to organization and method of operation, may be best understood by reference to the following description taken in conjunction with the subjoined claim and the accompanying drawings of which:

DETAILED DESCRIPTION OF THE INVENTION

Figure 1:
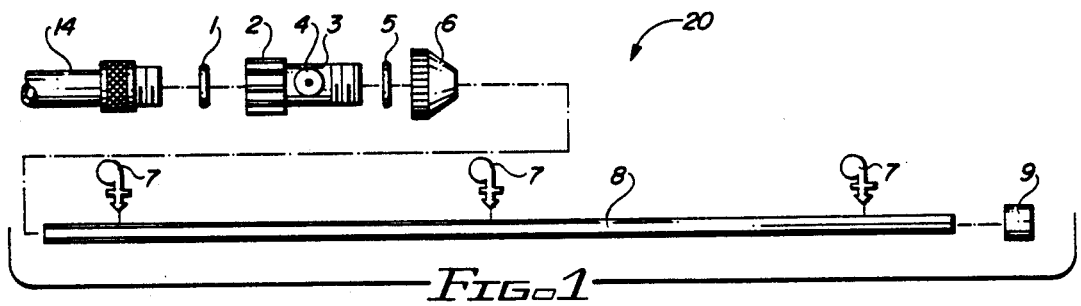
FIG. 1 is a pictorial representation of the misting device disassembled in sequential order, to show all component parts before assembly but not yet connected and attached to the lounging pad, in order to illustrate its general configuration.

Referring to FIG. 1 a common garden hose 14 is attached to misting device 20 by the female hose swivel 2 by means of threading together. A standard filtered washer 1 has two functions, one is to prevent unwanted particulates from entering the misting device, and the second is to provide a water tight connection. When pressured water is introduced into valve 3 it is controlled by valve lever 4. A standard rubber washer 5 is needed to maintain a water tight connection between valve 3 and tubing-to-valve adapter 6. Valve 3 and tubing adapter 6 are connected by means of threading the female end of the tubing adapter 6 on the male end of valve 3. The tubing adapter 6 also provides a water tight compression orifice when the polyethylene tubing 8 is inserted. Polyethylene tubing 8 is thereafter rotatably maintained within the compression orifice without water leakage from tubing adapter 6. The polyethylene tubing 8 is the conduit for the flow of water to the misting heads 7. At the distal end of polyethylene tubing 8 a tubing end cap connector 9 is provided to end-seal tube 8 to insure proper water pressure to misting heads 7.

Tubing end cap connector 9 has a compression orifice to maintain a water tight connection when poltethylene tubing 8 is inserted.

Figure 2:
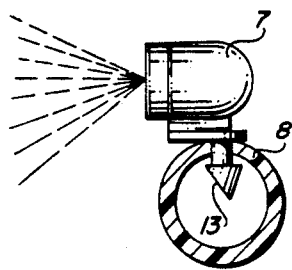
FIG. 2 is a pictorial representation of the misting head showing insertion of the pointed and notched stab lock fastener into the polyethylene tubing.

Referring to FIG. 2, misting heads 7 are designed so they can be inserted into the polyethylene tubing 8 by a pointed and notched stab lock fastener 13. They are placed at selected locations along polyethylene tubing 8. After misting heads 7 are inserted into polyethylene tubing 8 they can be horizontally hand rotated 360 degrees.

Figure 3:
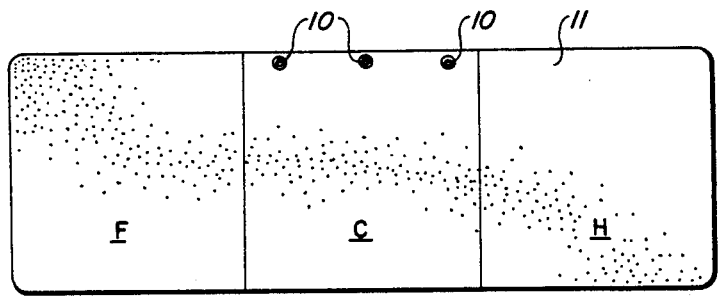
FIG. 3 is a pictorial representation of the multiposition lounging pad.

Referring to FIG. 3, the multiposition lounging pad 11 is illustrated to show its general configuration of sufficient length and width to contain the human body thereon. The length of pad 11 is comprised of three segmented portions: a head portion H, a center portion C, and, a foot portion F. As the drawing of FIG. 3 illustrates, each of these segments comprise approximately one-third the length of pad 11. The multiposition lounging pad 11 is made of mildew resistant foam rubber covered with a heavy duty waterproof vinyl. The rust resistant grommets 10 are part of the attachment means for securing the misting device to the multiposition lounging pad.

Figure 4:
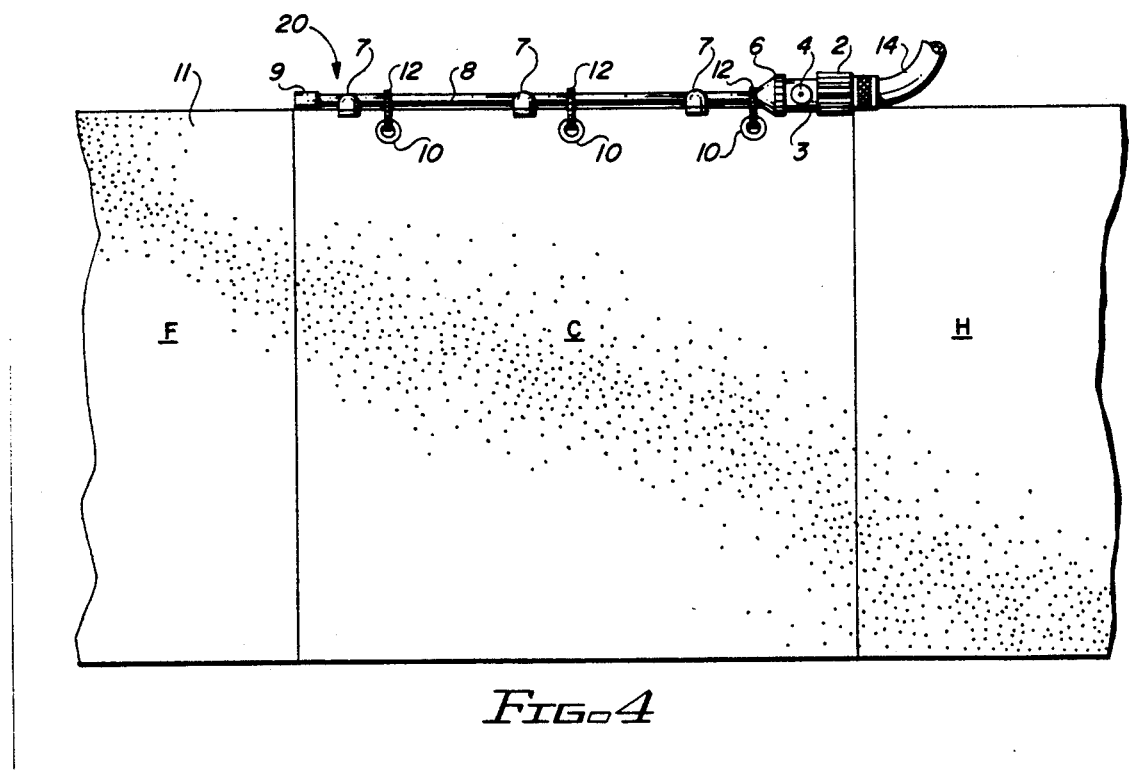
FIG. 4 is a pictorial representation of the misting device attached to the multiposition lounging pad providing for a multiposition misting lounging pad.

FIG. 4, shows the misting device attached to the multiposition lounging pad and secured by adjustable plastic straps 12 inserted through openings in rust resistant grommets 10. The misting device is positioned in the center portion C of the multiposition lounging pad 11 for fingertip control of valve lever 4. This positioning of the misting device allows for a perfect misting pattern for directing a fine gentle blanket of mist on a person lying on the multiposition misting lounging pad. This positioning also allows the opposite ends of the multiposition misting lounging pad to fold independently, for use in various applications including sunbathing chairs, lounges and most ground surfaces. Thus, while the principles of the invention have now been made clear in an illustrative embodiment, it will be immediately obvious to those skilled in the art many modifications of structure, arrangements, proportions, the elements, materials, and components, used in the practice of the invention which are particularly adapted for the specific environments and operating requirements without departing from those principles.

We claim:

1. In the combination of a lounging pad, on which a person may rest at least a part of his body, and a liquid spray device for spraying a person reclining on said pad, said liquid spray device being coupled along one side of said pad, the improvement comprising:

said pad being foldable into sections for ease of transport and storage, said liquid spray device being coupled along the side of one of said sections into which said pad is foldable and having a length generally equivalent to a side dimension of said section whereby said pad may be so folded for ease of transport and storage with said device being so coupled along said side of said one section;

said liquid spray device being a misting device comprising:

a selected length of liquid conduit tubing;

a misting head coupled to said length of liquid conduit tubing for emitting therefrom a fine, gentle mist when a pressurized source of liquid is coupled to said tubing; and means coupled to said liquid conduit tubing for adjustably and removably coupling said misting device to said lounge pad.

2. The improvement of claim 1 further comprising:

means for rotatably coupling said misting head to said liquid conduit tubing; and means for rotatably coupling said liquid conduit tubing to a source of pressurized liquid, whereby the direction of the emission of mist from said head may be selectably controlled.

* * * * *